United States Patent  
Alfano et al.

(10) Patent No.: US 10,281,331 B2  
(45) Date of Patent: May 7, 2019

(54) RESONANT STIMULATED RAMAN SCATTERING MICROSCOPE

(71) Applicants: Robert Alfano, New York, NY (US); Lingyan Shi, New York, NY (US)

(72) Inventors: Robert Alfano, New York, NY (US); Lingyan Shi, New York, NY (US)

( * ) Notice: Subject to any disclaimer, the term of this patent is extended or adjusted under 35 U.S.C. 154(b) by 0 days.

(21) Appl. No.: 15/904,089

(22) Filed: Feb. 23, 2018

(65) Prior Publication Data

US 2018/0238738 A1 Aug. 23, 2018

Related U.S. Application Data

(60) Provisional application No. 62/462,420, filed on Feb. 23, 2017.

(51) Int. Cl.
*G01J 3/44* (2006.01)
*G01J 3/10* (2006.01)
*A61K 49/00* (2006.01)
*H01S 3/30* (2006.01)

(52) U.S. Cl.
CPC .......... *G01J 3/4412* (2013.01); *A61K 49/006* (2013.01); *A61K 49/0013* (2013.01); *G01J 3/10* (2013.01); *G01J 3/44* (2013.01); *H01S 3/30* (2013.01)

(58) Field of Classification Search
CPC ... G01J 3/4412; G01J 3/10; G01J 3/44; A61K 49/0013; A61K 49/006; H01S 3/30
USPC ....................................................... 356/301
See application file for complete search history.

(56) References Cited

U.S. PATENT DOCUMENTS

2012/0200850 A1* 8/2012 Stewart .................. G01N 21/65  
356/301

OTHER PUBLICATIONS

C. V. Raman and K. Krishnan, Nature 121, 501 (1928).  
G. New, Introduction to Nonlinear Optics, Cambridge Press, p. 87-89, 186-188 (2011).  
R.L. Carman, MF Mack, F Shimizu, N Bloembergen, Phys. Rev. Lett. 23, 1327 (1969).  
E. J. Woodbury and WK Ng, Proc. IRE 50, 2367 (1962).  
J. B. Grun, A. K. McQuillan, and B. P. Stoicheff, Phys. Rev. 180, 61-68 (1969.) and JM Sparks, Phys. Rev. Lett, 32, 450 (1994).

(Continued)

*Primary Examiner* — Hina F Ayub  
(74) *Attorney, Agent, or Firm* — Myron Greenspan Lackenbach Siegel LLP

(57) ABSTRACT

A nonlinear optical process on increasing the signal in SRS microscope by Resonant Stimulated Raman Scattering (RSRS) combines both RRS and SRS nonlinear processes, in absorber and host such a β-carotene-methanol solution, Flavins, or other key absorbers in tissues. The observed effect of enhanced RSRS in small signal gain is attributed to RR process in absorber β-carotene that transferring excess vibrations to host methanol from anharmonic vibrational interactions between the solute β-carotene in resonance with the solvent methanol vibrations. SRS microscopy signals are improved in RSRS microscope for imaging vibrational states in lipids CH2 and proteins CH3 in cancer tissues from RR in Flavins or other native chromophores in tissue and for applications in other areas of neuroscience and biomedicine, potentially enhancing signals in the RSRS microscope by 2 to 1000 times.

26 Claims, 10 Drawing Sheets

(56) References Cited

OTHER PUBLICATIONS

R.L. Carman, F. Shimizu, C Wong, N. Bloembergen, Phys. Rev. A, 2, 60 (1970).
R.R. Alfano and SL Shapiro Phys Rev Letts 24, 592, 584, 1217 (1970).
M. Ji, S. Lewis, S. Camelo-Piragua, S. H. Ramkissoon, M. Snuderl, S. Venneti, A. Fisher-Hubbard, M. Garrard, D. Fu, A. C. Wang, J. A. Heth, C. O. Maher, N. Sanai, T. D. Johnson, C. W. Freudiger, O. Sagher, X. S. Xie and D. A. Orringer, Sci Transl Med. 7, 309ra163 (2015).
H. J. Butler, L. Ashton, B. Bird, G. Cinque, K. Curtis, J. Dorney, K. Esmonde-White, N. J. Fullwood, B. Gardner, P. L. Martin-Hirsch, M. J. Walsh, M. R. McAinsh, N. Stone and F. L. Martin, Nat Protoc. 11, 664-87 (2016).
C. W. Freudiger, W. Yang, G. R. Holtom, N. Peyghambarian, X. S. Xie and K. Q. Kieu, Nat Photonics 8, 153-159 (2014).
L. Wei, F Hu, Z Chen, Y Shen, L Zhang, and W Min Accounts of Chemical Research 2016 49 (8), 1494-1502 (2015).
F. Hu, Z. Chen, L. Zhang, Y. Shen, L. Wei and W. Min Angew. Chem. Int. Ed., 54: 9821-9825 (2015).
Peter Powers, Fundamentals of Nonlinear Optics, CRC Press (2011), p. 217-221, p. 49-54.
V.V. Kenkre, A. Tokmakoff, MD Fayer, J. Chem Phys, 101, 10618 (1994).
P. Moore, A Tomakoff, T Keyes , M.D. Fayer , J Chem Phys, 103, 3325, (1995).
K. Spanner, A Laubereau , W Kaiser , Chem Physics Lett , 44, 88 (1976).
A. Laubereau, L. Kirschner,, W Kaiser, Optics Comm 9, 182 (1973).

* cited by examiner

FIG. 8a
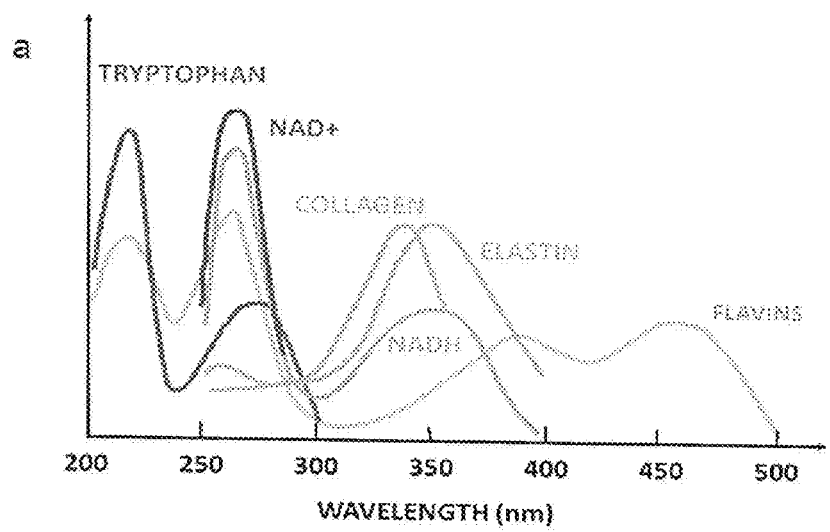
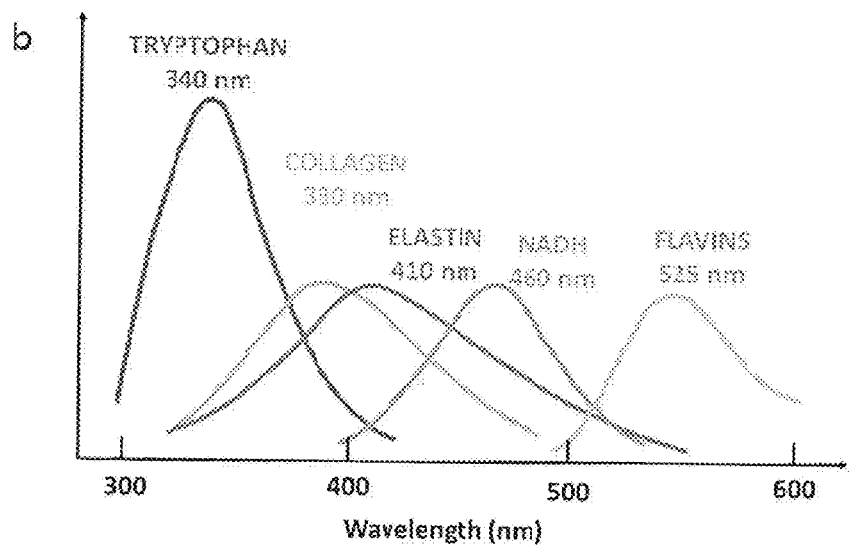
FIG. 8b

RESONANT STIMULATED RAMAN SCATTERING MICROSCOPE

BACKGROUND OF THE INVENTION

1. Field of the Invention

The invention generally relates to the field of microscopy and, more specifically, to Resonant Stimulated Raman Scattering Microscope.

A new non-linear optical (NLO) effect is disclosed, namely a Resonant Stimulated Raman Scattering (RSRS) effect for a new microscope arising from the excess vibrations generated from Resonant Raman (RR) processes in native (intrinsic) or extrinsic absorber, for example β-carotene or Flavins, transfer to its host media (say methanol) or tissues to excite the associated vibrations of the solutions or tissues via anharmonic vibrational interactions. This process leads to Raman gain in resonance to energy transfer from absorber and host vibrations, which are close to absorber, to host media solution or tissue. The Raman gain is enhanced from resonance of Raman cross section when pump photon frequency $\omega_L$ is in absorption or in wing near the emission wavelength of the intrinsic or extrinsic molecules to enhance the signal gain of the Stokes photon $\omega_s$ beam. The RSRS effect is important because it greatly increases the signal in stimulated Raman microscopy using RR of Flavins in the brain, breast, Cervix, skin, other organs and arteries. Using two beams, one at resonance of the molecules say at 532 nm or other visible pump laser light (i.e. 524 nm, 488 nm) and the other Stokes light beam (a tunable laser beam) at well defined vibrational shift of CH2, CH3 and amide 1 and tryptophan (amino acids) modes to get lipids and proteins vibrational lines in an image of the media—tissue, cell, or solution—for enhanced Stimulated Raman signal Gain at Stokes or Loss at pump laser in the microscope. Using objective lens with high NA, the beams are scanned by a scanner across the sample surface (x,y) and moved in depth z to get 2D or 3D plots of vibrational maps. The laser pump and tunable Stoke beam differ by the vibrational frequency $\omega_q$ to image, for example to detect and image biomolecules of glucose, tryptophan, amino acids, lipids, proteins, analytes, cholesterol in tissue, cells and bio fluids (urine and blood).

Resonant Raman Scattering (RSRS), combining both Resonant Raman Scattering (RRS) and Stimulated Raman Scattering (SRS) processes, generates a first new non-linear optical (NLO) effect.

The RSRS scattering process is at the heart of the new microscope for imaging and detecting changes associated with vibrations with disease. The observation of RSRS presented here is most important for new Stimulated Raman Loss (SRL) and Stimulated Raman Gain (SRG) microscopes in order to enhance signals of images from vibrations in biomedical tissues, cells fluids, and chemicals in the samples (ex vivo and in vivo). The selection of the pump or Stokes near an electronic resonance will improve the signal and the signal to noise ratio (i.e., S/N) of the SRS microscope image for tissues and cells from brain, breast, cervix, skin, arteries and in urine spinal, eye fluids and blood, etc.

2. Description of the Prior Art

Raman scattering is one of the key optical spectroscopic processes arising from inelastic scattering of light with vibrations in materials. The scattered light has a characteristic frequency shill due to vibrations accompanied by generation of optical phonons in the material. The Raman effect has been an active topic in various fields of science since its discovery in 1928 by Raman and Krishnan. The advent of laser in the 60's the Raman effect exploded in use. The Raman process occurs when a photon is scattered from a vibrational mode having its energy difference from the incident beam by the vibrational frequencies.

There are several different types of Raman processes that can occur, depending on the types of interactions between laser and matter, such as spontaneous, resonance, hyper Raman, and stimulated Raman. Spontaneous Raman (sR), despite being the weakest form of scattering, has widely been used as a powerful technique to investigate complex molecular and solid-state systems [2,3]. An enhancement of the Raman signal, essential for studies at low concentrations or in low cross section compounds, is achieved by Resonant Raman Spectroscopy (RRS), in which the laser excitation wavelength is tuned to match the energy of any electronic transitions of a system. Stimulated Raman scattering (SRS) can occur when Stokes photons are generated by gain of sR scattering in forward and backward with high pump lasers. SRS was first discovered when a cell with nitrobenzene was introduced inside a ruby laser cavity [4], where a rather strong emission at the wavelength other than the fundamental wavelength (694.3 nm) was observed. Stoicheff's group [5] measured various regions in Raman processes at different laser pump intensities of the first Stokes in nitrogen and oxygen liquids, namely R, small SRS gain, SRS, and SRS saturation [5], as the pump laser intensity was increased. Several researchers have demonstrated different Raman gains from transient to transient depending on the pulse duration and vibrational lifetime under picosecond (ps) pulses [6]. In the early 1970's, the 4 wave interactions producing the white light continuum and competing with SRS spanning the visible and part of NIR, now called supercontinuum (SC), was discovered by Alfano and Shapiro [7] in solids and liquids using ps-pulses.

Today, the use of SRS gain and loss (G/L) is active for imaging vibration of lipids, proteins and other molecules in biological and chemical materials such as brain, breast, biofluids, cells and cancer by injecting both light at wavelengths of the pump and Stokes wave together at the input [8-12].

In SRS microscopy, the sample is coherently driven by two lasers: one is the pump beam with frequency $\omega_L$ and the other is the Stokes beam with frequency $\omega_s$, where the difference is equal to a particular Raman-active molecular vibration of the sample. The SRS signals, including both stimulated Raman loss (SRL) at the laser pump beam and stimulated Raman gain (SRG) at the Stokes beam, are generated due to the nonlinear interaction between the photons and the vibration of the molecules [5, 6] for imaging [8-12]. The RSRS microscopy used either the pump or Stokes beam frequency to be in the electronic absorption band of the material for vibration enhancement via Raman cross section from the denominator poles. The development of novel nonlinear vibrational spectroscopy has allowed broadband SRS to provide high intensity coherent signal with low fluorescence background. In SRS, the sample is interrogated by a pair of overlapped narrowband picosecond (ps) Raman pulses and/or broadband femtosecond (fs) probe pulses. In SRS G/L process the vibrational spectrum, for example from lipids and proteins, occurs with the incoherent fluorescence background and the electronic susceptibility is efficiently suppressed. There is a need to sort out ways to increase the signal to noise (S/N) ratio in Stimulated Raman microscope that has been overlooked. Using Resonant Stimulated Raman scattering microscope occurs when one of the beam Pump or Stokes photons is it resonance with molecule electronic states to enhance the SRS cross section effect. In addition S/N is improved by higher frequency modulation that reduces the 1/f noise and dark current. The Stokes beam for ps/fs sources are created from the pump laser beam by OPO, OPA, or SHG to reduce jitter time effects between the pump and Stokes beams.

SUMMARY OF THE INVENTION

The present invention is directed to a novel nonlinear optical process on increasing the signal in an SRS microscope by Resonant Stimulated Raman Scattering (RSRS), which combines both RRS and SRS nonlinear processes in absorber and host such a β-carotene-methanol solution, Flavins or other key absorbers in tissues, cell, or biofluid. An example is a carotene-methanol solution to demonstrate the effect using pump beam at the second harmonic generation (SHG) from a Q-switched Nd:YAG laser. In this manner the Raman signals are increased. The observed effect of enhanced RSRS in small signal gain is attributed to RR process in absorber β-carotene that transfers excess vibrations to the host methanol from anharmonic vibrational interactions between the solute carotene in resonance with the solvent methanol vibrations. This discovery of RSRS is important toward improving SRS microscopy signals in RSRS microscope for imaging vibrational states in lipids CH2 and proteins CH3 in cancer tissues from RR in Flavins or other native chromophores in tissue and for applications in other areas of neuroscience and biomedicine. Using one or more beams in near resonance the RR feeds and the other Stokes beam from coupling via vibrations serves to enhance the signal in the RSRS microscope by 2 to 1000 times. The most intensive Raman scattering bands for SRS Raman gain or Raman loss are located at 1450 $cm^{-1}$, 2850 $cm^{-1}$ (CH2 stretching) and 2950 $cm^{-1}$ (CH3 stretching). Other well-pronounced bands are 1240 to 1280 $cm^{-1}$ (C—N stretching), 1300 to 1340 $cm^{-1}$ (CH2 twisting, wagging of bending), 1540 to 1580 $cm^{-1}$ (C—C deformation mode, tryptophan), and 1640 to 1680 $cm^{-1}$ (C—O stretching, amide). Evidences from clinical and experimental data indicate that neurodegenerative disorders and cancers usually have a coexisting metabolic dysfunction, which can directly correlate to changes in proteins in tissue or body fluids. For example, cancer is known to have a hallmark of upregulation of glucose uptake, and protein/lipids metabolism, due to its rapid cell dividing. Alzheimer's diseases (AD) has a significant large amount of amyloid beta proteins deposit in patient's brain. These protein's secondary structure or amide is potentially detectable by this RSRS method, which shed light on disease detection at earlier stage.

BRIEF DESCRIPTION OF THE FIGURES

The above and other aspects, features and advantages of the present invention will be more apparent from the following description when taken in conjunction with the accompanying drawings, in which:

FIG. 7b is a schematic diagram of the RSRS microscope shown in FIG. 7a;

FIG. 8a illustrates absorption curves of native molecules in tissues and cells; and FIG. 8b illustrates emission curves of the native molecules in FIG. 8a in tissues and cells.

DETAILED DESCRIPTION

Figure 1:
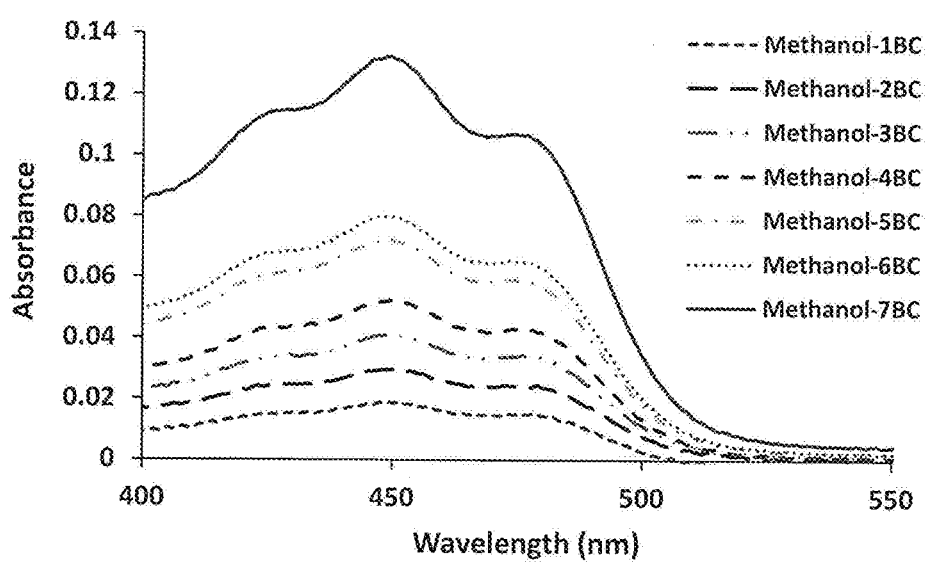
FIG. 1 illustrates the absorbance versus wavelength for an extracted solution from a 20 cm glass cell tube into 1 cm test sample.

FIG. 1 shows how peak intensities of the first Stokes (1S) resonance peaks increase with absorption at 450 nm of β-carotene in methanol solution up to a certain limit. The SRS signal increases with increasing absorption up to a certain limit (i.e., 0.06) due to RSRS mechanism.

The absorbance attains peak value is at wavelength 450 nm and it increases with increasing concentration of β-carotene solution in methanol. β-carotene concentration increases from "1BC" to "7BC".

To show the RSRS effect, the relationship is first determined between absorbance of β-carotene in methanol and wavelength as well as the enhancement of the Raman scattering by resonance, using a Cary 500 UV-VIS NIR Spectrophotometer. Flavins have similar absorbance peak at about 500 nm with emission at about 530 nm. We found that the absorbance increases with the increase of β-carotene concentration, it reaches the peak at about 450 nm and the absorbance tail extends to 550 nm (FIG. 1) for all carotene concentrations. Then using the absorption tail wavelength 532 nm as the pumping laser with an Ocean Optics Raman microscopy, we perform spontaneous Raman on methanol and β-carotene in methanol to identify the salient peaks of methanol and β-carotene in methanol, as the results shown in FIG. 2a. When there is no β-carotene in methanol (dash-line, FIG. 2a), the most significant Raman peaks of methanol occur at 2834 $cm^{-1}$ and there are minor peaks at 1035 $cm^{-1}$ and 1425 $cm^{-1}$, respectively. The Raman peaks of interest from β-carotene solution occur at 1525 $cm^{-1}$, 1157 $cm^{-1}$ and 2834 $cm^{-1}$ from methanol, respectively. At low concentration of β-carotene (10 drops, solid line, FIG. 2a), the peak intensities at around 1525 $cm^{-1}$ and 1157 $cm^{-1}$ have increased and the peak at around 2834 $cm^{-1}$ has decreased slightly; while at high concentration of β-carotene (59 drops, dash-dot line, FIG. 2a), peaks at around 1525 $cm^{-1}$ and 1157 $cm^{-1}$ are now most intense, while the peak at 2834 $cm^{-1}$ has decreased considerably.

Figure 2A:
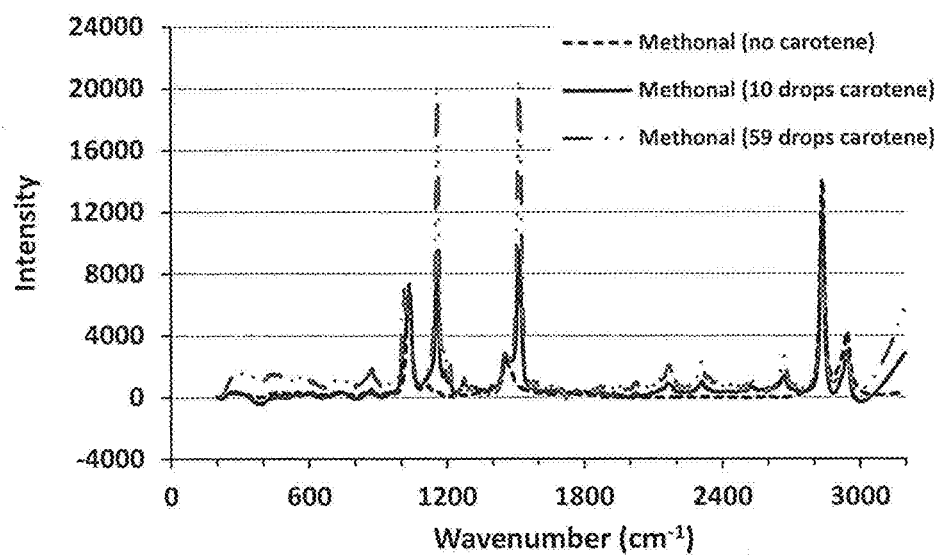
FIG. 2a illustrates Resonant Raman intensity at different concentrations of β-carotene and, specifically, Resonant Raman spectra of methanol solution containing different concentrations (drops) of β-carotene.
Figure 2B:
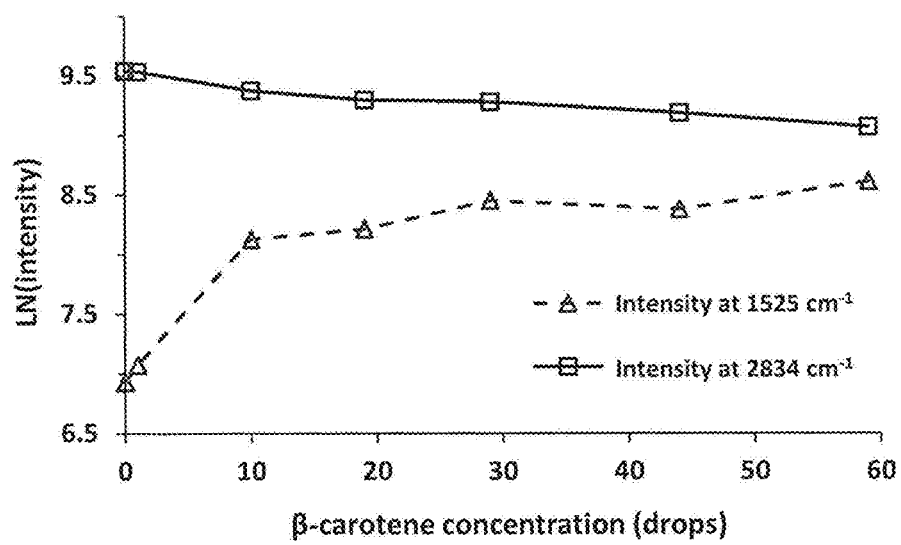
FIG. 2b illustrates the relationship between the intensity at Raman, peaks (1525 $cm^{-1}$ and 2834 $cm^{-1}$) and β-carotene concentration. The intensity is plotted in natural logarithm. The intensity at 1525 $cm^{-1}$ (dashlines) increases about 4-fold and the intensity at 2834 $cm^{-1}$ (solid line) decreases slightly with β-carotene concentration.

FIG. 2b shows the relationship. between the intensity of the Raman peaks and β-carotene concentration at wavenumbers 1525 $cm^{-1}$ and 2834 $cm^{-1}$ that were observed in FIG. 2a. The intensities of the peaks at 1525 $cm^{-1}$ increased with the concentration of β-carotene solution in methanol, and consequently the absorption (also called optical density, OD) of the solution increased. It was found that the intensity of Raman peaks of β-carotene became amplified by the Resonant Raman effects, which is observed in Raman spectra. The intensity of the peak at 2834 cm$^{-1}$ decreased when the absorption of the solution increased as a result of adding β-carotene solution; however, it did not fall as sharply as would be predicted by exponential Lambert Beer's Law but instead decreased algebraically, suggesting that an interaction between methanol solvent molecules and the β-carotene molecules exists thereby showing a slight increase of 2834 cm$^{-1}$ mode with the addition of β-carotene solution. The 1525 cm$^{-1}$ (and 1157 cm$^{-1}$) modes from carotene and from the methanol or carotene bath can provide the vibrations to produce more modes at 2834 cm$^{-1}$ from methanol. Similar effect in tissues was observed using RR from vibration coupled to native flavins and other chromophores in tissue such as collagen, elastin, and NADH.

Figure 3:
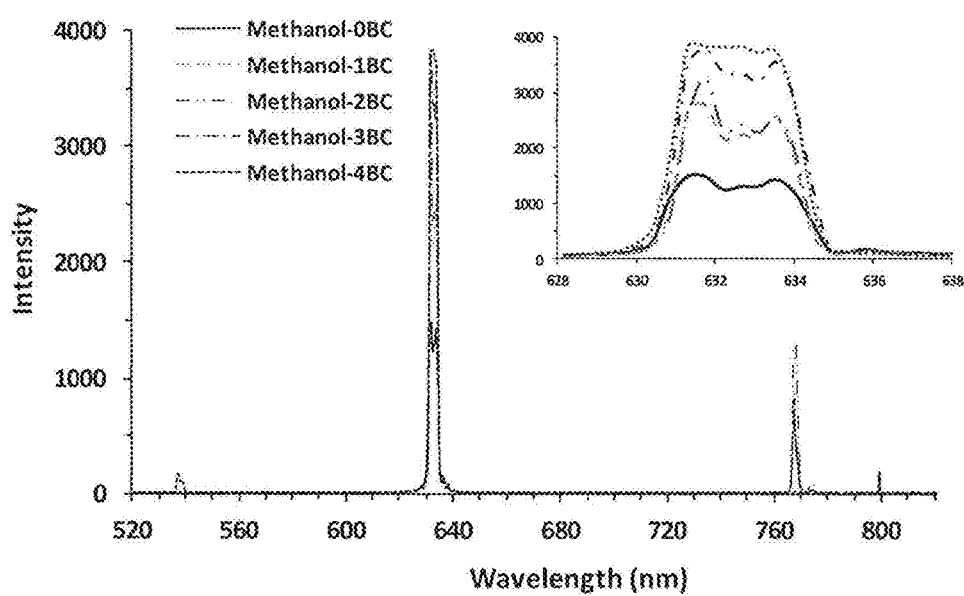
FIG. 3 illustrates the effects of Resonant Stimulated Raman Scattering (RSRS) as a function of wavelength.

To show the RR effect Resonance Simulated Raman scattering (RSRS) was performed on β-carotene in methanol using a Q-switched Quanta Ray Nd:Yag laser with the pumping wavelength 532 nm. The RSRS spectra of β-carotene in methanol was successfully obtained at different concentrations (FIG. 3). As the concentration of carotene is increased, the signal intensity of the 1S at 632 nm increases and at higher absorption the second Stokes (2S) appears (~770 nm). The Raman signals are shifted by the CH3 vibrational mode of methanol at wavenumber 2834 cm$^{-1}$ (shown in FIG. 2a). At higher carotene concentration the SRS signal grows at the same input excitation wavelength 532 nm.

The appearances of 1S and a second peak (2S) are marked by increasing the concentration of β-carotene in methanol solution, when excited by high power pulsed laser beam. "0BC" denotes no β-carotene, and β-carotene concentration increases from "1BC"-"4BC". The upright corner in FIG. 3 shows intensities at the amplified wavelength region 628-638 nm.

Figure 4:
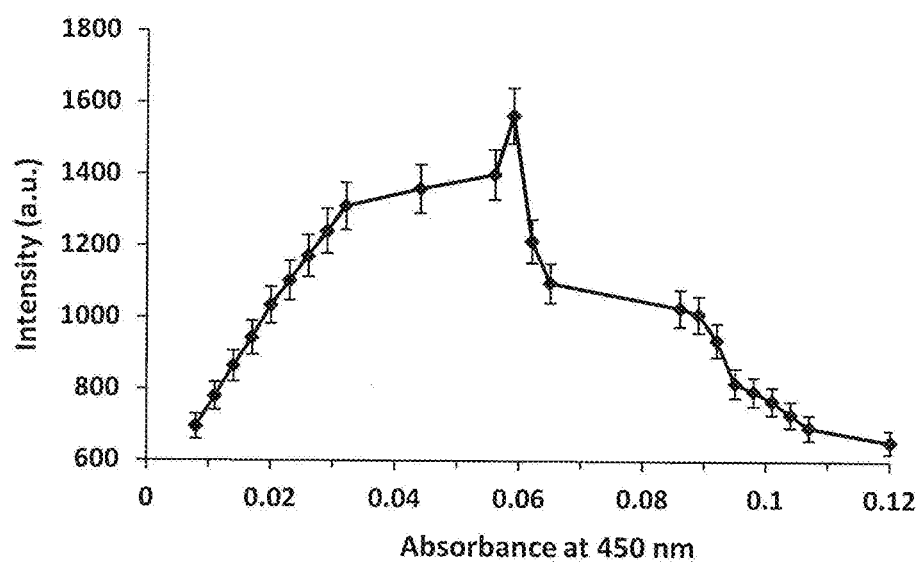
FIG. 4 illustrates the profile of first Stokes (1S) Raman intensity versus absorption (OD)

FIG. 4 shows how peak intensities of the 1S resonance peaks increase with absorption at 450 nm of β-carotene in methanol solution up to a certain limit. The SRS signal increases with increasing absorption up to a certain limit (i.e., 0.06) due to RSRS mechanism.

FIG. 4 shows that the SRS signal initially increases linearly with the absorption of carotene. At absorption 0.03 it flattens most likely from generation of the second singlet state ($S_2$), and after absorption 0.06 the SRS signal decreases due to too much absorption. The addition of carotene absorption shows the SRS intensity is enhanced due to resonance behavior that producing RSRS effects at 1S and at higher absorbance 2S appears of methanol (as shown in FIG. 3) with the intensity increase of the 2834 cm$^{-1}$ mode. The observation of RSRS is important, as it has its applications in new versions of SRS microscopes for imaging vibrations from the sample using RSRS loss and gain mechanisms.

In this demonstration RSRS, β-carotene provides the methanol solution with the necessary enhancement of cross-section in the visible where the absorption peaks at 450 nm extending out beyond 532 nm. The main absorption of β-carotene is from $S_2$ state since the $S_1$ state is dipole forbidden. The concentration of β-carotene was varied from a stock 10$^{-4}$ M by added drops with neat methanol liquid.

The salient features of the example of β-carotene RSRS observations include that
1) the SRS occurs at methanol frequencies due to the presence of carotene;
2) carotene absorption is from $S_2$ state with little fluorescence;
3) carotene and methanol are combined coupled material. The vibration of the solute enhances the interaction of the solution via Fermi Golden rule from density of states ρ of solute, solvent, and solute-solvent coupling. RSS occurs from methanol CH3 bond at 2834 cm$^{-1}$, but not at a vibration mode from carotene; and
4) Raman resonance seems to occur in frequency part of the cross section at 532 nm in out resonance with little self absorption at Stokes frequencies.

The key observation of this study is that the carotene solute influences vibrations of methanol. The solute-solvent system can have different interactions: vibrations between solute molecules, solvent molecules, or solute and solvent molecules [14, 15, 16, 17]. There is a coupling as shown in spontaneous Raman at 2834 cm$^{-1}$ (FIG. 2a). There is a slight increase in spontaneous Raman signal at 2834 cm$^{-1}$ with more than 20 drops from an exponential decreasing behavior. Anharmonic coupling between solute and solvent from solvation of shells accounts for the relaxation of excited solvent and solute molecules. The conservation of energy affects the relaxation of a vibration. If there is no energy match the vibration is long, and if there is a match among the vibrations the decay is fast. In Fermi Golden rule for rate among states of interaction is from square of Hamiltonian from anharmonic terms, and the density of final states ρ available. The latter term ρ is the main process to determine the system process from solute-solvent, solvent, and solute states [2, 14, 15, 16, 17]. The anharmonic coupling allows for the flow of energy among the vibrational modes. A cubic anharmonicity allows for excitation of the solute and solvent vibration modes to be exchanged during interaction. A quartic anharmonicity exchange corresponds to vibration and bath phonon exchange.

Vibrational energy processes in binary solvent A and solute B system can have cubic and quartic interactions [14]. A possible quartic interaction in methanol solvent from resonance Raman of carotene is the 1525 cm$^{-1}$ and 1157 cm$^{-1}$ modes that generates 2834 cm$^{-1}$ and deactivate 150 cm$^{-1}$ methanol bath phonons, such as 1525 cm$^{-1}$+1157 cm$^{-1}$→2834 cm$^{-1}$-150 cm$^{-1}$ [A*A*B*B goes to AABB*].

Figure 5:
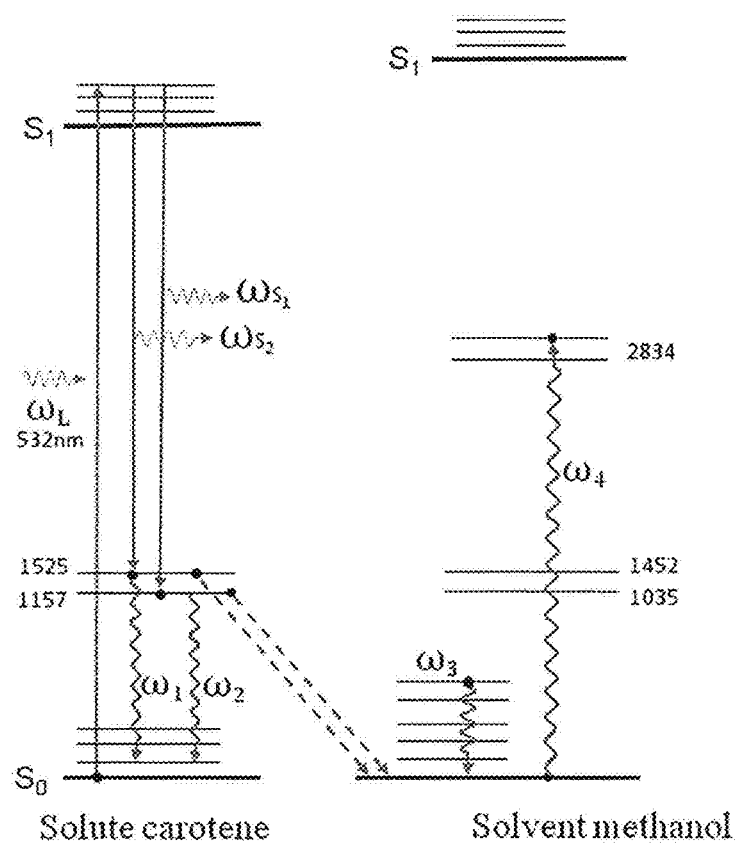
FIG. 5 illustrates a schematic of vibrational modes of β-carotene and methanol.

FIG. 5 shows a schematic energy diagram of the potential quartic vibrations attributing to the enhancement of SRS at 2834 cm$^{-1}$ mode, involved in resonance Raman of carotene (see supplements for background theory in more detail). As FIG. 5 shows, a possible model where upon excitation by 532 nm, carotene undergoes RR scattering at 1525 cm$^{-1}$ and 1157 cm$^{-1}$ and then transfer energy to methanol with bath phonons from methanol to excite the methanol mode at 2834 cm$^{-1}$. The data in FIG. 2 supports the energy transfer model from carotene to methanol at 2834 cm$^{-1}$.

In the past Kasier's group [16, 17] investigated cubic interactions, one excited molecule say A* decays though resonant and non-resonant interaction in cubic collisions: A*AA, A*AB, and A*BB. These cubic interaction affects the vibration lifetime decay. Kaiser and coworkers [16, 17] observed the cubic interaction of higher vibration CH3 with addition of another liquid of CCl$_4$. The vibration lifetime of A* of CH3 increases with more of B. Therefore the Raman gain will become larger with addition of CCl$_4$ going from transient gain to steady state gain. Raman gain will increase towards more steady state-like when lifetime of the vibrations become longer. This effect will be more important using femtosecond and picosecond pulses, but not nanosecond pump laser pulse. So here the resonance of B (i.e., carotene) to A (i.e., methanol) will be the major cause for RSRS process.

The solute carotene affects the transfer of vibrations (1525 cm$^{-1}$+1152 cm$^{-1}$) of the resonance to solvent methanol (M) (2834 cm$^{-1}$ and phonon bath) in a quartic interaction (C1*C2*M1*M2), thereby enhancing the cross section. A theoretical analysis following [14] on the underlying physics is needed to explain the RSRS process observed from the vibrations of solute carotene and solvent methanol. Time resolved femtosecond pump-probe may be used to test and determine the energy transfer speculative mechanism present here.

The discovery of RSRS may be important toward improving SRS microscopy signals for imaging vibrational states in lipids and proteins in cancer and areas of neuroscience and biomedicine. To implement the observed effect to the RSRS microscope the pump laser needs to be in the absorption wing, for example, at 532 nm to be in resonance with tail of the absorption of the tail Flavins peak at 500 nm in tissues and cells and tunable probe laser to 570 to 650 nm to probe the SR gain of either CH2 band for lipids, and CH3 bands for proteins in the 2850 and 2930 cm$^{-1}$, respectively.

RSRS combines both RRS and SRS processes to provide a first new non-linear optical (NLO) effect. The observation of RSRS is most important for new Stimulated Raman Loss (SRL) and Stimulated Raman Gain (SRG) microscopes in order to enhance signals of images from vibrations in biomedical tissues, cells and chemicals in samples. The selection of the pump or Stokes near an electronic resonance will improve the signal to noise ratio (i.e., S/N) of the SRS microscope image for tissues and cells from brain, breast, arteries etc Referring to FIG. 5, arrows indicate transitions for cubic and quantic interactions. There is an energy transfer of vibrational states from carotene solute to surrounding methanol solvent by dash lines and skewed lines.

Method Example

β-carotene powder was dissolved into methanol and was added gradually into 20 cm optical cell holding methanol solution to study its effects. 1-cm glass cells were used to collect solution and measure the optical density of the dissolved carotene in methanol in the 20-cm cell after intensity profile was captured from the 20-cm cell, while firing the cell with the laser.

Figure 6:
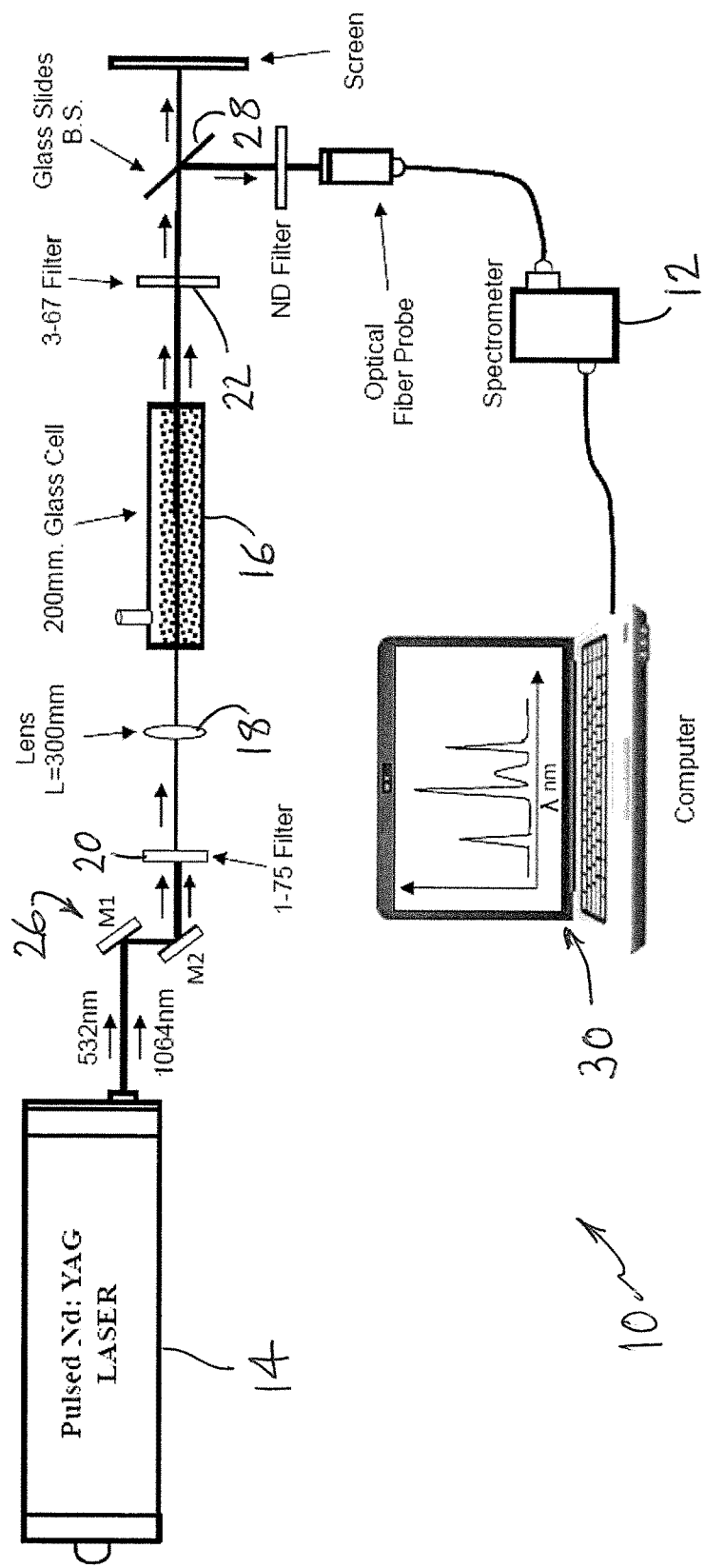
FIG. 6 is a schematic of a conventional Resonant Stimulated Raman Scattering (RSRS) experimental setup.

The conventional setup 10 is shown in FIG. 6. A Cary 500 UV-VIS NIR Spectrophotometer 12 was used for measuring the absorbance, and an Ocean Optics Raman microscope was used to capture Resonance Raman (not shown here) spectra. For RSRS experiments, a Q-switched Quanta Ray Nd:YAG laser of 1064 nm laser beam (with SHG KDP crystal) 14 provides a laser excitation beam at 532 nm. The power was set to produce about 10 mJ per pulse at a pulse duration of 5 ns. A 20-cm glass cell tube 16 was used to hold a methanol solution with β-carotene for the Stimulated Raman Scattering (SRS) experiments. A converging lens 18 of focal length 30 cm was used to focus the laser beam onto the cell 16. One 1-75 filter 20 was used to block the 1064 nm laser light before the laser beam impinged upon the cell holding methanol solution, and two 3-67 color filters 22 were used in front of the spectrometer to block the last trace of 532 nm laser beam. An Ocean Optics spectrometer 12 was used to detect the Stimulated Raman (SR) spectra. Neutral density filters 24 were used to adjust SRS signal at input to spectrometer to avoid the saturation of the SRS signals arising from the pump beam's interaction of the β-carotene solution with methanol.

While β-carotene has been used in the example other materials can be used including, but not limited to, Indocyanine green (ICG), sodium-fluorescein, chlorophyll, flavins), antibodies, dimers, antibody fragment, nanoparticles, nanotubes engineered fluorescent proteins, optogenetic proteins, etc.

Referring to FIG. 6, the conventional RSRS setup includes:

M; Mirrors 26; L: Lens; 1-75 Filter 20: to filter-out the 1064-nm laser beam; Glass-Cell 16: to hold methanol and β-carotene solution; 3-67 Filter 22: to filter out 532-nm laser beam; BS: Beam-splitter (glass-slide) 28; spectrometer 12 with computer 30: to capture signal generated by laser-methanol (plus β-carotene) interaction.

Background Theory

The intensity of the spontaneous Raman (sR) is weak ($10^{-6}$ $I_L$) [7], where $I_L$ is the laser intensity. The power scattered is given by $$P_s = N\left(\frac{\partial \sigma}{\partial \Omega}\right)_R \Delta \Omega I_L = N\sigma_R I_L, \qquad (1)$$

where the cross-section is given by:

$$\sigma_R = \left(\frac{\partial \sigma}{\partial \Omega}\right)_R d\Omega, \qquad (2)$$

and N is the number of molecules in the observed volume and $$\left(\frac{\partial \sigma}{\partial \Omega}\right)$$

is the differential Raman cross-section.

When the excited laser wavelength approaches an electronic absorption in a material, the transitions among the states go from virtual to real. The Raman scattering signal becomes enhanced due to the resonant effect. The enhancement in the cross section arises from the energy denominator of nonlinear susceptibility [9], see Eq 3, becoming small as the laser frequency matches the electronic energy states. The virtual transition of the intermediate state becomes real and Raman effect becomes larger by 10 to 1000 folds, depending on how close the laser photon energy is in the transit from the ground state (i) to electronic state (j). The Raman intensity increases when either the in resonances or out resonances occur with the pump and Raman shifted light with the electronic states. This process is called Resonance Raman scattering (RRS) [2, 13].

The Raman cross-section for single molecule is given by:

$$\sigma_R = \left|\sum \frac{A_{iijf}}{(\omega_{ij} - \omega_L - i\Gamma_j)} + \frac{A_{jijf}}{(\omega_{jf} - \omega_L - i\Gamma_j)}\right|^2 \qquad (3)$$

for in and out resonances. When $\omega_L$ approaches $\omega_{ij}$, the denominator reduces and $\sigma^R$ increases and Raman becomes resonant Raman scattering (RRS). The frequency dependence of cross section in Eq. 3 shows the salient resonance features between the pump and probe frequency with electronic absorption for enhancement.

When an intense laser pulse (such as ns, ps, fs) enters a material, the Raman effect occurs. The light is first scattered over large angle Ω. As the Raman light travels with the pump laser in the forward and backward directions it can become larger than the Raman light traveling out of the beam at other angles as it propagates with laser pulse and over a length of more than 10 cm. Depending upon the intensity of the laser pump pulse the Raman light in the forward and backward directions may become so large that it can be stimulated and become laser-like with high direction and coherence.

The intensity of Raman Stokes gain in SRS is given by a Beer-Lambert's law-like equation [13]:

$$I_{RS}(z)=I_{RS}(0)\exp(Gz-\alpha z), \quad (4)$$

where G is the gain, $\alpha$ is the loss, and $I_{RS}(0)$ is initial Stokes from zero point fluctuation which has SR at z=0.

The Raman gain G is given as $$G = N\left(\frac{\partial \sigma}{\partial \Omega}\right)I_L \Delta \Omega \quad (5)$$

In any SRS, the Raman gain must exceed the loss due to absorption in the media, where Gz>25 and the medium will experience an exponential growth of photon at Stokes frequency. The Raman light in the forward direction becomes much greater than spontaneous Raman and becomes SRS with about 1% to 10% of energy transferred from pump frequency. For small SRS gain Eq. 4 reduces to $$I_{RSR}=I_{RS}(1-Gz)a \quad (6)$$

and the SRS signal difference is $$\Delta I_{SRS}=AI_{RS}I_L z \quad (7)$$

where A is a constant. There is loss at laser and gain at the Stokes called RSRS again. The power of the pump and Stokes beams can be provided CW diode lasers, tunable lasers, or picosecond lasers based on TiS or Yb (ytterbium) optical fiber lasers and OPO or OPA (sources are available from APE and Coherent lasers) with an average power of >5 millwatts focus to a spot size of about 1 to a few micrometers using a microscope objective lens of 20× to 60×. This gives a >0.5 MW/cm² intensity (power per area, P/A) in the low SRS gain regime. One pump laser enters the wing of the native absorber in tissue for RR to probe SRL and the other probes Stokes laser for the vibration for SRS gain for RSRS.

The observation of Raman gain in FIG. 4 for 2834 cm⁻¹ vibration mode for binary solution of solvent (methanol, M) with solute (carotene, C) is attributed to Resonant Raman (RR) of the solute C with vibrational energy transfer from C to excite M vibration via anharmonic interactions as depicted in FIG. 5.

The following gives a model of the generation of the excess of excited vibrations by RR and energy transfer from C to M. In support of the proposed model, an order of magnitude calculation follows to explain the observed Raman small gain of M from the excess of M vibration cm⁻¹ with the increase C concentration and in turn more absorption from C molecules from RR effect of C molecules.

The size of sR intensity is about:

$$I_{sR}=10^{-6}I_L$$

and resonance Raman intensity is given by $$I_{RR} \sim 10^{-3} I_L \text{ to } 10^{-2} I_L$$

The RR process generating excess vibrations is similar to the number created by SRS. The number of photons for the pump laser of 5 mJ of 5 ns duration at 532 nm is $$N_L \sim 1.26 \times 10^{17} \text{ photons}$$

The number of carotene vibration modes (nc) created via RR is smaller by $10^{-3}$-fold:

$$nc=(10^{-3})(1.26\times 10^{17})=1.26\times 10^{14} \text{ vibrations}$$

The excitation laser volume V from beam diameter of about 100 μm in length of about 2 cm is:

$$V=2\times 10^{-4} \text{ cm}^3$$

So, the number of excited vibrations per cm³ from RR is:

$$nc=(1.26\times 10^{14})/(2\times 10^{-4})=0.6\times 10^{18} \text{ vibrations/cm}^3$$

The number of molecules per volume of a liquid is about $5\times 10^{21}$/cm³. The total number of carotene molecules for $10^{-4}$ Molar solution gives the number of carotene molecules as:

$$Nc=(5\times 10^{21})(10^{-4})=5\times 10^{17} \text{ carotene molecules/cm}^3$$

The occupation number of carotene vibrations at 2834 cm⁻¹ in excess of the thermal number is:

$$nc(C \text{ vibration})=Nc \text{ vibrations}/Nc \text{ molecules}=(0.6\times 10^{18}/\text{cm}^3)/(5\times 10^{17}/\text{cm}3)$$

$$nc=1.2$$

which is larger than thermal occupation numbers of $$n_T=10^{-6} \text{ for 3000 cm}^{-1} \text{ modes and } n_T=10^{-2} \text{ for 1000 cm}^{-1} \text{ modes}$$

In the vibration energy transfer of carotene vibrations with efficient $\eta=10^{-2}$ from carotene to methanol gives occupation number for methanol vibrational occupation of $$n_0(\text{methanol})=1.2\times 10^{-2}$$

which is still greater than the thermal occupations for 3000 cm⁻¹ modes. Even if $\eta=10^{-5}$, the $n_0$ of excess methanol vibrations is $>n_T$.

The vibration excitation of methanol from RR of carotene over the thermal occupation mode at 3000 cm⁻¹ is $$n_0/n_T=1.2\times 10^{-2}/10^{-6}=1.2\times 10^4$$

which is greater than thermal by 12,000 times and the M vibrations is hot.

This model provides a way to describe the buildup of methanol from RR of carotene vibrational modes. The rate equation governing the population of methanol vibration $n_M$ from energy transfer from carotene $n_C^*$ to methanol with efficiency of transfer $\eta$ given by:

$$dn_M/dt=-n_M/T_1+\eta n_C^*/T_0$$

where $T_1$ is depopulation relaxation time on M, and $T_0$ is the repopulation relaxation time of excited RR carotene. The first term is the decay of methanol occupation vibration $n_M$ and the second term is for feeding M.

The steady state occupation of the methanol is given by $$n_M=\eta n_C^* T_1/T_0$$

The RR enhance small signal gain of methanol, from Eq. 7, becomes:

$$\Delta I_{SRSR} \sim g I_L I_S z = n_M \sigma I_L I_S z.$$

The cross section gives the enhancement of the RSRS signal.

RSRS Microscope

Figure 7:
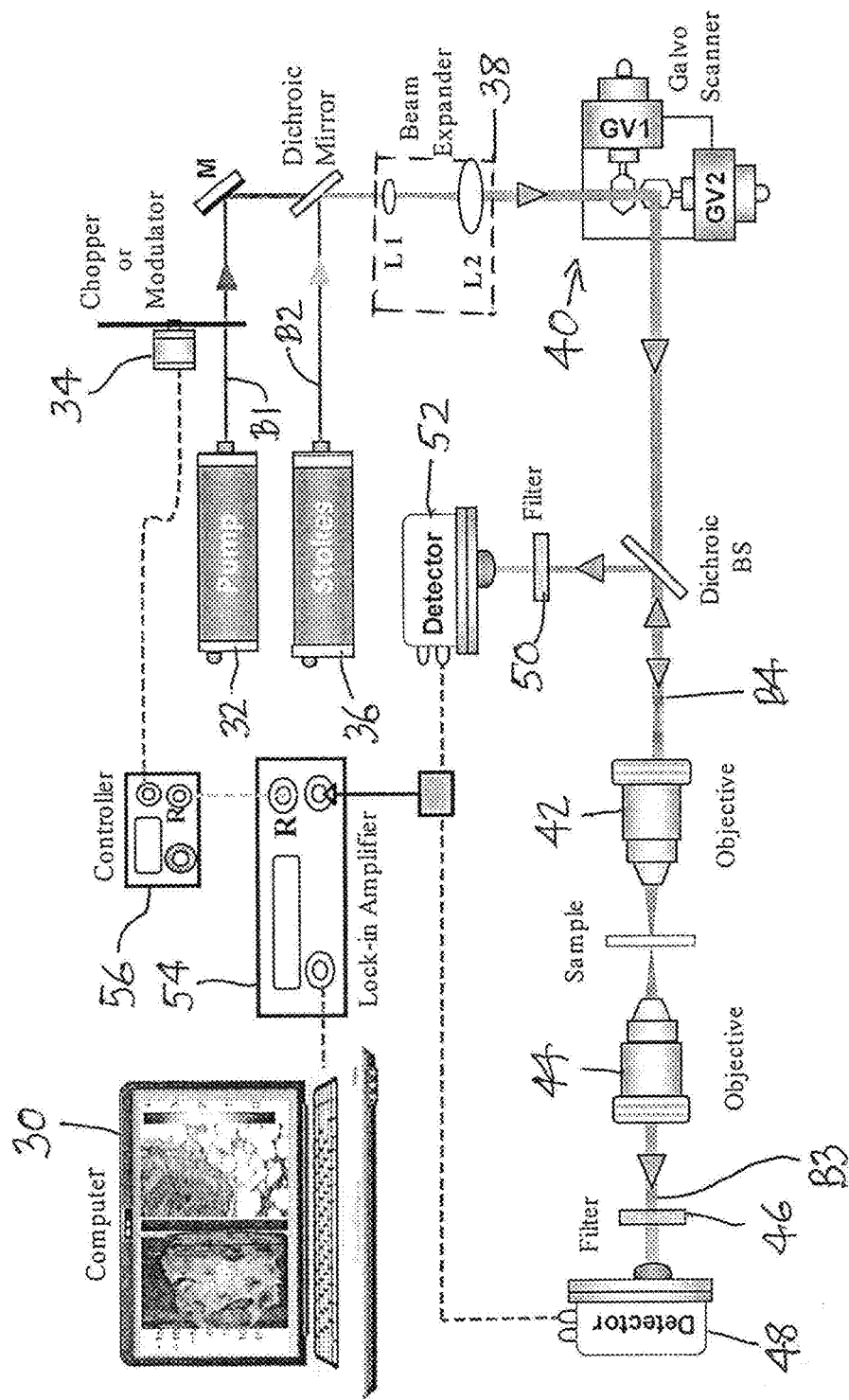
FIG. 7 illustrates one embodiment of an RSRS microscope with pump wavelength near absorption of sample and probe Stoke shifted by vibration frequency.

FIG. 7 shows the main components of the design of a RSRS microscope in accordance with this invention, forming two lasers beams B1, B2 by one laser (the pump) 32 modulated by a chopper or modulator 34 near the absorption frequencies of Flavins, collagen, elastin, or NADH and the other laser (tunable) 36 or fixed array of diode lasers with wavelengths at various Raman shifts of CH2, CH3, amide, tryptophan, and or other key vibrations modes for chemicals biofluids (urine/blood/eye fluid) and analytes images in 2D and 3D using a beam expander 38 and a scanner 40. The beams B1 and B2 are directed through an objective 42 at the sample. For forward detection (normally for thin samples) the beam B3, after passing through an objective 44, passes through a filter 46 that transmits the Stokes signals that are detected by a detector 48. For backward detection (normally for thicker samples) the beam B4, after passing through an objective 42, passes through a filter 50, again to transmit the Stokes signals that are then detected by a detector 52. The detectors 48, 52 provide signals to the lock-in amplifier 54 that is used to detect the Resonant Raman Gain (SRG) of the Stokes wave at the modulation frequency of the pump beam B1 or SRL at the pump frequency. A controller 56, using a signal from the lock-in amplifier 54, controls the chopper or modulator 34.

One can detect SRL at higher signal change instead of SRG because the responsivity of the photodiode used is higher for the pump than for the Stokes beam. Collinear pump- and Stokes-beams B1, B2 are focused with a high numerical aperture objective 42 onto a common focal spot of the sample (FIG. 7). To detect the pump- or Stokes-beams in the forward direction a condenser 44 with a numerical aperture higher than that of the excitation objective 42 is used, in order to minimize unwanted background due to XPM (cross-phase-modulation), which yields background noise. The backward and forward detection nodes are possible in turbid samples because multiple scattering events redirect a significant portion of the forward propagating pump and Stokes beams to the backward direction, which can be collected with the same excitation objective lens. The Stokes is not near absorption that is resonant caused by the pump laser.

Figure 7A:
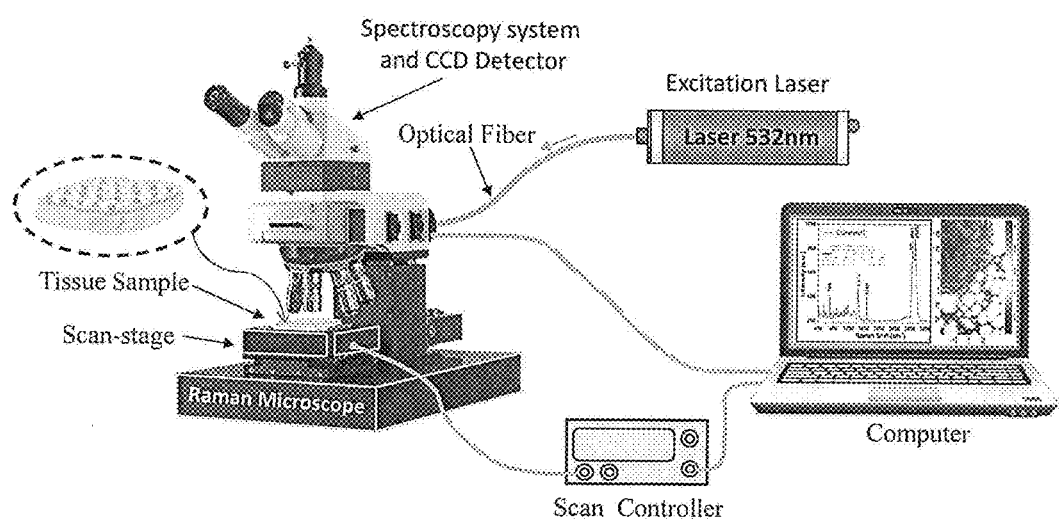
FIG. 7a illustrates another embodiment of an RSRS microscope that utilizes a single beam ps/fs laser to generate both pump and Stokes beams.
Figure 7B:
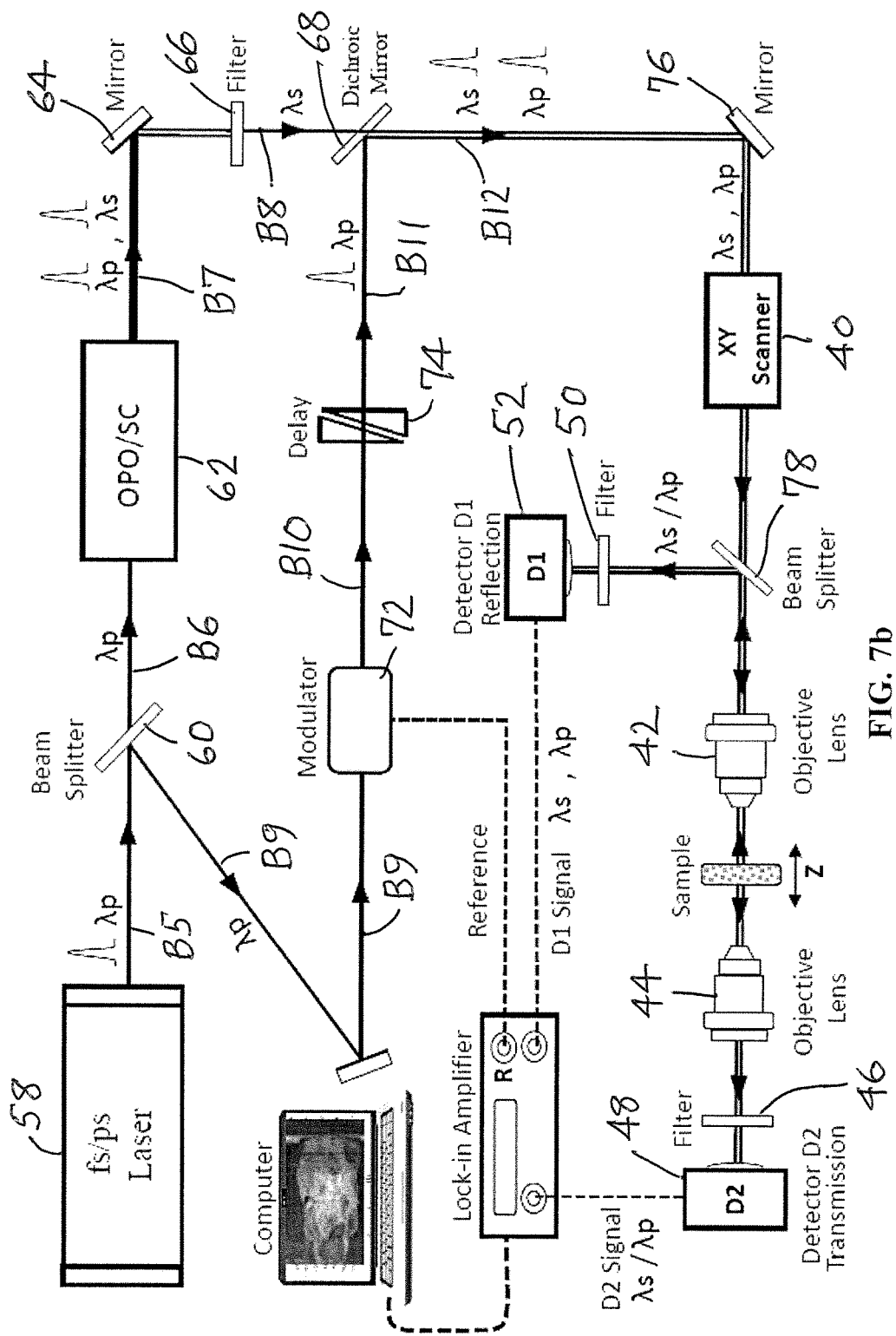

Referring to FIGS. 7a and 7b, an alternate embodiment of an RSRS microscope is illustrated that utilizes a single source laser. In FIG. 7b the laser is a ps/fs laser designated by the reference numeral 58. The laser 58 generates a pump pulse $\lambda_p$. The beam B5 is transmitted through a beam splitter 60, the pulse frequency appearing as beam B6 input to optical parametric oscillator 62. The output of the unit 62 are pulses representing the pump frequency as well as Stoke frequency or continuum beams B7. The beams are directed by mirror 64 to a filter array 66 that allows the Stoke beam or signals to pass, forming beam B8 that passes through dichroic mirror 68. The pump frequency beam B5 is redirected by the beam splitter 60 to form a pump beam B9 that is reflected off mirror 70 and directed to modulator 72. The pump beam B9 emanates from the modulator 72 as beam B10 directed to a timing delay element 74 the purpose of which is to synchronize the pump and Stoke pulses at the dichroic mirror 68 where both the pump and Stoke beams B8 and B11 are combined as beam B12 that is, in turn, reflected by mirror 76 to the x-y scanner 40. As in the previous embodiment, the modulator provides a reference signal to the lock-in amplifier 54. The operation of the detectors 48 and 52 is substantially as previously described.

FIGS. 8a and 8b show the absorption and emission spectra of key molecules that are in tissues and in some cells to undergo optical pumping by pump laser and by Stokes laser to probe associate vibrations to under stimulate Raman gain in resonant for RSRS effect with vibrations that are coupled to the native chromophores'. The power of the pump and Stokes beams in FIG. 7 can be from CW diode lasers or picosecond lasers (Nd:Yag/SHG or Yb:Fiber laser/SHG), Optical parametric Oscillator (OPO), or amplifiers (OPA) with an average power of >5 to 200 milliwatts focused to a spot size at sample of about 1 to a few micrometers using a microscope objective lens of 20× to 60×. This gives a >0.5 to 20 MW/cm$^2$ intensity (power per area, P/A) in the small SRS gain signal regime.

While the invention has been shown and described with reference to certain embodiments thereof, it will be understood by those skilled in the art that various changes in form and detail may be made therein without departing from the spirit and scope of the invention as defined by the appended claims and their equivalents.

REFERENCES (1) C. V. Raman and K. Krishnan, Nature 121, 501 (1928).
(2) G. New, Introduction to Nonlinear Optics, Cambridge Press, p 87-89, 186-188 (2011).
(3) R. L. Carman, M F Mack, F Shimizu, N Bloembergen, Phys. Rev. Lett. 23, 1327 (1969).
(4) E. J. Woodbury and W K Ng, Proc. IRE 50, 2367 (1962).
(5) J. B. Grun, A. K. McQuillan, and B. P. Stoicheff, Phys. Rev. 180, 61-68 (1969.) and J M Sparks, Phys. Rev. Lett, 32, 450 (1994).
(6) R. L. Carman, F. Shimizu, C Wong, N. Bloembergen, Phys. Rev. A, 2, 60 (1970).
(7) R. R. Alfano and S L Shapiro Phys Rev Letts 24, 592, 584, 1217 (1970).
(8) M. Ji, S. Lewis, S. Camelo-Piragua, S. H. Ramkissoon, M. Snuderi, S. Venneti, A. Fisher-Hubbard, M. Garrard, D. Fu, A. C. Wang, J. A. Heth, C. O. Maher, N. Sanai, T. D. Johnson, C. W. Freudiger, O. Sagher, X. S. Xie and D. A. Orringer, Sci Transl Med. 7, 309ra163 (2015).
(9) H. J. Butler, L. Ashton, B. Bird, G. Cinque, K. Curtis, J. Dorney, K. Esmonde-White, N. J. Fullwood, B. Gardner, P. L. Martin-Hirsch, M. J. Walsh, M. R. McAinsh, N. Stone and F. L. Martin, Nat Protoc. 11, 664-87 (2016).
(10) C. W. Freudiger, W. Yang, G. R. Holtom, N. Peyghambarian, X. S. Xie and K. Q. Kieu, Nat Photonics 8, 153-159 (2014).
(11) L. Wei, F Hu, Z Chen, Y Shen, L Zhang, and W Min Accounts of Chemical Research 2016 49 (8), 1494-1502 (2015).
(12) F. Hu, Z. Chen, L. Zhang, Y. Shen, L. Wei and W. Min Angew. Chem. Int. Ed., 54: 9821-9825 (2015).
(13) Peter Powers, Fundamentals of Nonlinear Optics, CRC Press (2011), p 217-221, p 49-54.
(14) V. V. Kenkre, A. Tokmakoff, M D Payer, J. Chem Phys. 101, 10618 (1994).
(15) P. Moore, A Tomakoff, T Keyes, M. D. Fayer, J Chem Phys, 103, 3325, (1995).
(16) K. Spanner, A Laubereau, W Kaiser, Chem Physics Lett, 44, 88 (1976).
(17) A. Laubereau, L. Kirschner, W Kaiser, Optics Comm 9, 182 (1973).

The invention claimed is:

1. A method of analyzing the structure of a material in a host solution comprising the step of using Resonant Stimulated Raman Scattering (RSRS) effect to generate excess vibrations created from resonant Raman (RR) processes from electronic transitions in at least one solution absorber.

2. A method as defined in claim 1, wherein the solution resides in living tissue.

3. A method as defined in claim 2, wherein said at least one solution absorber comprises at least one of Flavins, NADH, Collagen or Elastin transfer to the associate vibrations of CH2 (lipids), CH3 (protein), amide and/or tryptophan.

4. A method as defined in claim 3, wherein key molecules are pumped in tissue of Tryptophan (at 265 nm to 300 nm), Collagen (at 320 nm to 380 nm), Elastin (at 340 nm to 440 nm), NADH (at 340 nm to 480 nm), DNA (at 230 nm to 270 nm) and Flavins (at 400 nm to 532 nm) for resonant SRG of the associate vibrations.

5. A method as defined in claim 3, wherein beam wavelengths in key molecules are pumped in cells of Tryptophan (at 265 nm to 300 nm), NADH (at 400 nm to 480 nm), Flavins (at 400 nm to 532nm), and DNA and RNA (at 230 nm to 270 nm) for resonant SRG of the associated vibrations.

6. A method as defined in claim 1, wherein excitation leads of absorber to Raman gain in resonance to energy transfer from absorber and host vibrations, which are close to absorber, to host media solution or tissue.

7. A method as defined in claim 1, wherein two bearers are used, one at resonance of molecules, say from 350 nm to 514.5 and 532 nm, or other visible pump laser light, and the other Stokes light beam (a tunable laser) covering 500 nm to 800 nm at well defined vibrational shift of CH2, CH3 and amide 1 and tryptophan modes to get lipids, and proteins vibrational lines in an image of the media—tissue, cell or solution for enhance Stimulate Raman signal Gain at Stokes or Loss at pump laser in the microscope.

8. A method as defined in claim 7, wherein the pump and Stokes beams are scanned by a scanner across the sample surface (x,y) and moved in depth a to get 2D or 3D plots of vibrational maps of the Lipids, Proteins, Amino acids of tissue and/or cell sample.

9. A method as defined in claim 5, wherein the laser beams can be from 340 nm to 2500 nm from UV, visible, NIR, SWIR.

10. A method as defined in claim 7, wherein RSRS uses Supercontinuum to generate pump and Stokes beams, the wavelengths of Supercontinuum or white light lasers ranging from 340 nm to 2580 nm for creating apparatus for resonance Stimulates Raman Scattering spectroscopy or RSRS microscope.

11. A method as defined in claim 7, wherein one pump laser enters the wing of native absorber in tissue for RR and the pump beam probes Stimulated Raman Loss (SRL) and the Stokes beam probes the vibration for SRS gain for RSRS.

12. A method as defined in claim 1, wherein RSRS combines both Resonant Raman Spectroscopy (RRS) and stimulated Raman Scattering (SRS) processes.

13. A method as defined in claim 1, wherein the material is one of ex vivo and in vivo living tissue.

14. A method as defined in claim 13, wherein the tissue is one of brain, breast, cervix, skin, arteries and organs.

15. A method as defined in claim 1, wherein said host solution is formed by introducing absorbers into a host, such as various dyes (carotene, ICG, sodium-fluorescein, chlorophyll, flavins), antibodies, dimers, antibody fragment, nanoparticles, nanotubes engineered fluorescent proteins, optogenetic proteins, etc.

16. Apparatus for analyzing the structure of a sample of a material in a host solution, comprising beam generating means for generating pump and Stokes beams; scanning means for scanning said beams and directing said beams at said sample; using Resonant Stimulated Raman Scattering (RSRS) effect to generate excess vibrations created from resonant Raman (RR) processes from electronic transitions in at least one solution absorber.

17. Apparatus as defined in claim 16, comprising two laser beams, one laser the pump near the absorption peak or wing of amino acids, flavins, collagen, elastin, or NADH, and the other the Stokes tunable laser or fixed array of diode lasers with wavelengths at various Raman shifts to see enhance gain at CH2, CH3, Amide, tryptophan, and/or other key vibrations modes by Raman Stokes lasers and Loss by Laser pump source for chemicals and analytes images in 2D and 3D using a scanner for in vivo or ex vivo.

18. Apparatus as defined in claim 17, wherein said laser beams are substantially within the range of 340 nm to 2500 nm from UV, visible, NIR, SWIR.

19. Apparatus as defined in claim 17, wherein said pump laser is at 532 nm and the Stokes laser is within the range of 560 nm-700 nm.

20. Apparatus as defined in claim 16, wherein said pump and Stokes beams are selected to appear near an electronic resonance to improve the S/N ratio.

21. Apparatus as defined in claim 16, wherein said scanning means comprises a scanner to move beams onto the sample of the SRS microscope image for tissues and cells from brain, breast, cervix, skin, arteries and other organs, etc.

22. Apparatus as defined in claim 16, wherein said beam generating means comprises a source of supercontinuum to generate said pump and Stokes beams.

23. Apparatus as defined in claim 16, wherein power of the pump and Stokes beams are provided from CW diode lasers, tunable lasers or picosecond lasers (such as Ti:sapphire, Nd:Yag/SHG or Y:Fiber laser/SHG, OPO or OPA) with an average power of >5 to 200 millwatts focused to a spot size at sample of about 1 to a few micrometers using microscope objective lens of 20× to 60× to provide a >0.5 to 20 MW/cm$^2$ power intensity (power per area, P/A) in the small SRS gain signal regime.

24. Apparatus as defined in claim 16, wherein RSRS uses a picosecond laser from APE Emerald laser or Coherent Monaco laser with 2 SHGs for the pump Yb (Yetterbium) optical fiber and probe OPO or OPA for RSRS for wavelengths from 516 nm, 1032 nm and tunable 760 to 900 nm.

25. Apparatus as defined in claim 16, wherein RSRS uses a picosecond/femtosecond Ti:sapphire laser with SHG, OPO or OPA for RSRS sources for wavelengths from 500 nm and tunable 700 to 1000 nm and SHG 350 nm into 500 nm.

26. RSRS microscope for analyzing the structure of a sample of a material in a host solution, comprising beam generating means for generating pump and Stokes beams; scanning means for scanning said beams and directing said beams at said sample; using Resonant Stimulated Raman Scattering (RSRS) effect to generate excess vibrations created from resonant Raman (RR) processes from electronic transitions in at least one solution absorber.

* * * * *